United States Patent
Mueller et al.

(10) Patent No.: US 7,007,829 B1
(45) Date of Patent: Mar. 7, 2006

(54) HOLLOW HANDLE PUSH-UP PISTON FOR A FOOD CONTAINER

(75) Inventors: Martin J. Mueller, Oldsmar, FL (US); Richard W. Mueller, Oldsmar, FL (US)

(73) Assignee: Chief Packaging Company, LLC, Oldsmar, FL (US)

( * ) Notice: Subject to any disclaimer, the term of this patent is extended or adjusted under 35 U.S.C. 154(b) by 223 days.

(21) Appl. No.: 10/370,241

(22) Filed: Feb. 19, 2003

(51) Int. Cl.
*B67D 5/42* (2006.01)

(52) U.S. Cl. ............ 222/386; 222/129; 222/136; 426/115

(58) Field of Classification Search ......... 222/386, 222/136, 129.2, 129–130, 325–327, 386.5, 222/1; 426/120, 115, 124, 130; 366/129, 366/256, 332, 289
See application file for complete search history.

(56) References Cited

U.S. PATENT DOCUMENTS

| | | | | |
|---|---|---|---|---|
| 2,786,769 A | * | 3/1957 | Greenspan | 426/117 |
| 3,348,546 A | * | 10/1967 | Roberts et al. | 604/89 |
| 3,370,754 A | * | 2/1968 | Schumann et al. | 222/132 |
| 3,420,417 A | * | 1/1969 | Kardel | 222/390 |
| 3,459,296 A | * | 8/1969 | Berg | 206/229 |
| 3,464,412 A | * | 9/1969 | Schwartz | 604/89 |
| 3,489,147 A | * | 1/1970 | Shaw | 604/88 |
| 3,659,749 A | * | 5/1972 | Schwartz | 222/129 |
| 3,707,146 A | * | 12/1972 | Cook et al. | 600/593 |
| 3,735,900 A | * | 5/1973 | Gores | 222/129 |
| 4,676,406 A | * | 6/1987 | Frischmann et al. | 222/136 |
| 4,826,047 A | * | 5/1989 | Heflin | 222/136 |
| 6,231,904 B1 | * | 5/2001 | Mueller | 426/112 |
| 6,261,611 B1 | * | 7/2001 | Berman | 426/90 |

* cited by examiner

Primary Examiner—Frederick Nicolas
(74) Attorney, Agent, or Firm—Mathew R. P. Perrone, Jr.

(57) ABSTRACT

A dessert container has a tube with a piston. The piston includes a food contact member slidably mounted in the tube. The piston also has a hollow rod extending from and suitable for use with the food contact member. With the piston thus mounted in the tube, wherein the hollow rod can apply pressure to the food contact member for the piston, food may be forced out of the end of the tube, which is oppositely disposed from the piston.

9 Claims, 3 Drawing Sheets

HOLLOW HANDLE PUSH-UP PISTON FOR A FOOD CONTAINER

This invention relates to a push-up piston for a food container; and more particularly to a hollow handle push-up piston for a dessert or other food contained in a cylinder.

BACKGROUND OF THE INVENTION

Commonly, material such as food or ice cream can be contained within a tube. At one end of the tube is a piston. The other another end of the tube is openable. When the tube is opened, the piston may force the food contained therein out of the tube and permit consumption of the exposed food.

The piston or plunger forces the food out of the tube and permits efficient consumption of the food from the tube. The tube contains the food in an efficient fashion until consumption thereof is desired. Such procedures are relatively common for foods, which may slide within a tube. These tubes are especially useful for foods, which soften with heat. A typical food, which softens with heat is ice cream.

The plunger or piston usually has a support device such as a stick or a rod to assist with the movement of the food through the tube toward the openable end. This rod is utilitarian and serves no other function. It is extremely difficult to modify the stick or rod to have an additional function.

SUMMARY OF THE INVENTION

Among the many objectives of this invention is the provision of a hollow handle supporting a piston slidably mounted in a tube containing a food.

A further objective of this invention is the provision of a releasable hollow handle supporting a piston slidably mounted in a tube containing a food.

A still further objective of this invention is the provision of a food within a releasable hollow handle.

These and other objectives of the invention (which other objectives become clear by consideration of the specification, claims and drawings as a whole) are met by providing a food container having a tube with a piston. The piston includes a food contact member slidably mounted in the tube. The piston also has a hollow handle extending from and suitable for use with the food contact member. With the piston thus mounted in the tube, wherein the hollow handle can apply pressure to the food contact member for the piston, food may be forced out of the end of the tube, which is oppositely disposed from the piston.

BRIEF DESCRIPTION OF THE DRAWINGS

Throughout the figures of the drawings, where the same part appears in more than one figure of the drawings, the same number is applied thereto.

DESCRIPTION OF THE PREFERRED EMBODIMENTS

In a disposable dessert or other food dispenser or container, there is a tubular member or tube for holding a firstfood, with a piston or plunger (which terms may be used interchangeably herein) at one end of the tube and a releasable closing member at the other end of the tube. On the piston or plunger is a hollow handle, which may contain a second food. Thus, the food container of this invention includes a tube with a piston or plunger mounted therein. With the releasable closing member removed, the piston or plunger may be pushed further into the tube and force the food contained therein out of the openable end, so that the food contained in the tube may be consumed. In this manner two food compartments are provided therein.

The first food and the second food may be the same or different. Preferably, the first food is softenable food such as ice cream or yogurt. The first food must be movable when pressure from the plunger is applied. The second food is preferably a solid food, in small pieces, which will pour out of the hollow handle. Many types of candy fit this description. Other with similar physical properties, and similar or different compositions may be used.

The tubular member may be of any suitable shape so long as the piston is receivable therein. Customarily, the desired shape is cylindrical. Accordingly, the piston is shaped to correspond to an interior diameter of the tubular member, such that the piston may slide therethrough and force food within the tubular member out of the member for consumption.

The piston includes a food pushing member with a hollow handle extending therefrom. The hollow handle has a closed end and an open end. The hollow handle is generally tubular in shape. The open end of the hollow handle is secured in the base of the plunger in a central holder thereof. An apertured tab extends downwardly from the central holder. Adjacent the open end of a hollow handle are male protuberances. These male protuberances each have an aperture in the tab which may receive the same. Such an action holds the hollow handle in the central holder. By lifting the tab, the male protuberances are released, thereby permitting removal of the hollow handle from the central holder and consumption of candy or other food which may be stored therein.

Figure 1:
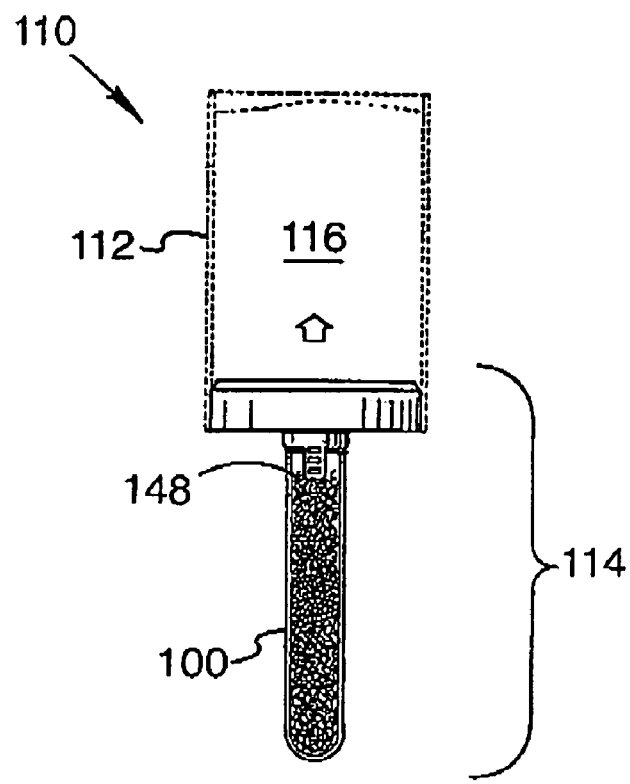
FIG. 1 is a side view of the hollow handle 100 of this invention.

Referring now to FIG. 1, hollow handle 100 is incorporated into a dessert dispenser 110. The dessert dispenser 110 includes a tubular member 112 with the piston or plunger 114 mounted therein. Within the tubular member 112, is an appropriate food 116. Food 116 may be ice cream, yogurt, or another suitable food capable of being expelled from the tube.

Figure 2:
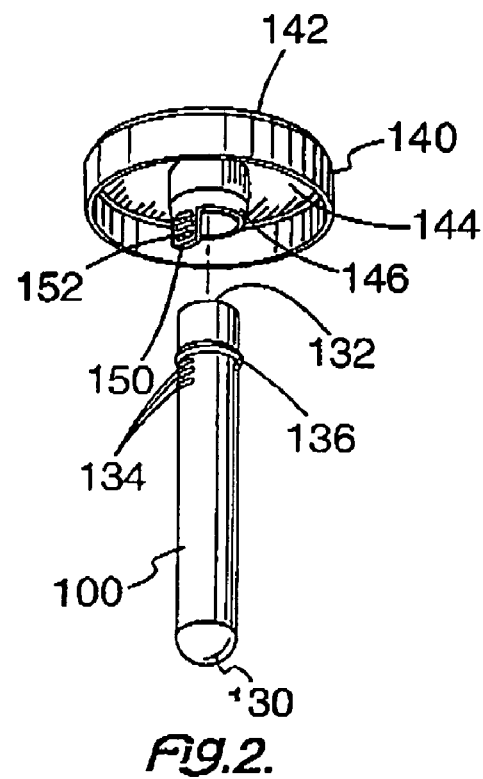
FIG. 2 depicts a perspective exploded view of the hollow handle 100 of this invention.
Figure 3:
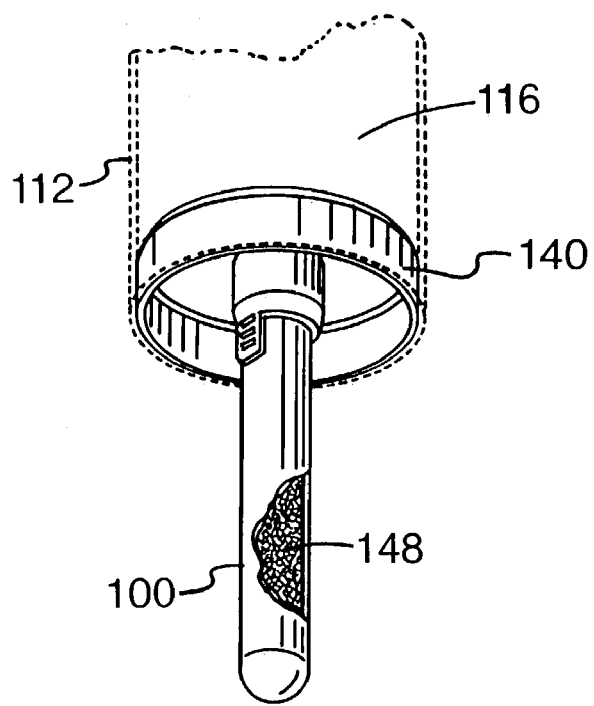
FIG. 3 depicts a perspective assembled view of the dessert dispenser 100 with hollow handle 100 of this invention.

Adding FIG. 2 and FIG. 3 to the consideration, the structure of the hollow handle 100 becomes more clear. The hollow handle 100 has a closed end 130 and an open end 132 oppositely disposed therefrom. Adjacent to the open end 132 are three protuberances 134.

The plunger 114 includes a food pushing member 140, which is completed when the hollow tube 100 is releasably secured thereto. More particularly, the food pushing member 140 of plunger 114 has a food side 142, which contacts food 116 contained within the tubular member 112. Oppositely disposed from food side 142 is pushing side 144. Centrally in located pushing side 144 is central holder 146.

Central holder 146 is adapted to receive the open end 132 of hollow handle 100 in a female to male relationship in order to thereby close open end 132. As open end 132 is closed, a second food 148 of the appropriate size may be contained therein prior to sealing therein. Seat support 136 is adapted to contact central holder 146 and seal hollow handle 100 thereon. Central holder 146 is cylindrical in nature.

Extending from central holder 146 is an apertured tab 150. Open end 132 mounts slidably in the central holder 146 is a male female relationship. Apertured tab 150 extends downwardly from central holder 146 and includes an aperture 152 for each of the male protuberances 134, in order to provide a snap locking mechanism to hold hollow handle 100 and central holder 146 and hence food pushing member 140. Each aperture 152 in tab 150 has a matching male protuberance 134. Other locking mechanisms are of course operable.

Figure 4:
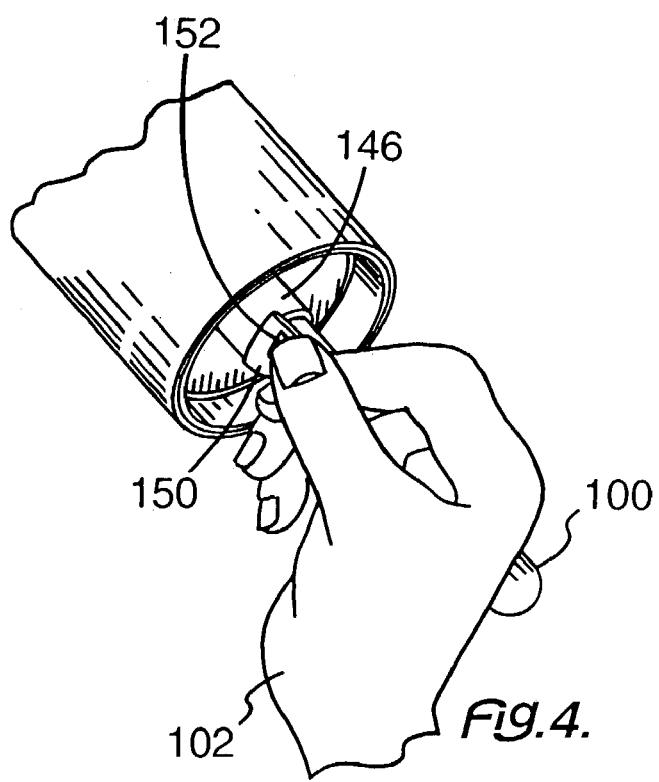
FIG. 4 depicts a perspective assembled view of the hollow handle 100 of this invention showing a released mechanism.

With the consideration of FIG. 4, hand 102 is shown as operating apertured tab 150. As apertured tab 150 is lifted by hand 102, male protuberances 134 are freed from tab apertures 152 and permit removal of hollow handle 100 from central holder 146. Then second food 148 may be consumed through open end 132.

Figure 5:
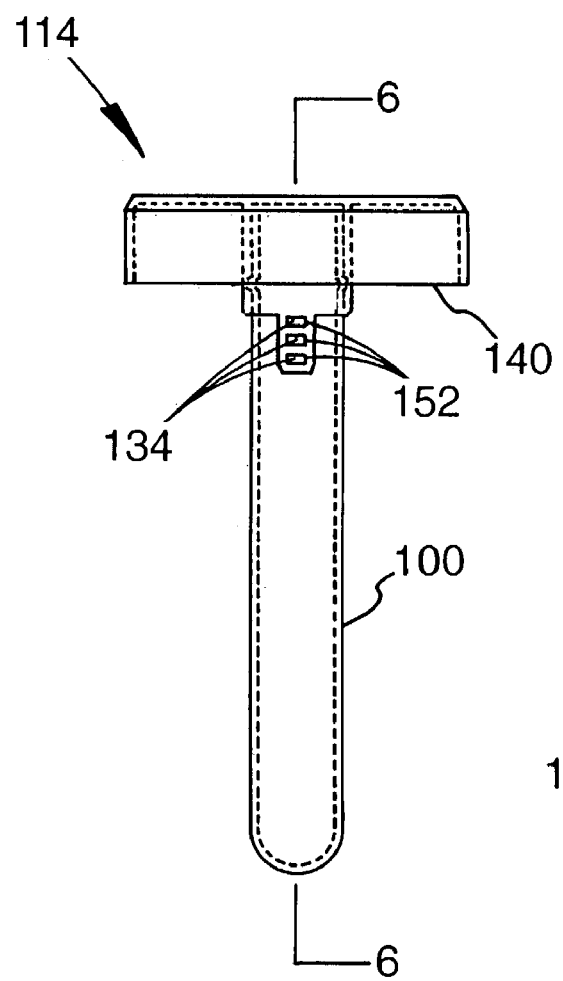
FIG. 5 depicts a side assembled view of the hollow handle 100 of this invention.
Figure 6:
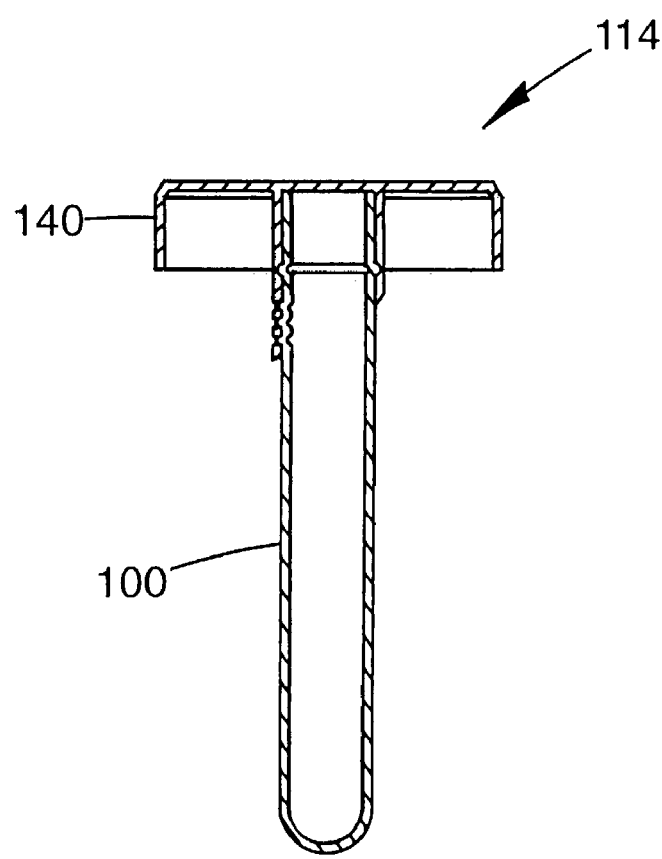
FIG. 6 depicts a side cross-sectioned view of the hollow handle 100 of this invention.

FIG. 5 and FIG. 6 even more clearly set out the structure of hollow handle 100 and cooperation of hollow handle 100 with food pushing member 140 in order to form plunger 114. Tab apertures 152 cooperate with male protuberances 134 to hold hollow handle 100 and a proper position. In this fashion, plunger 114 is efficiently formed.

This application—taken as a whole with the specification, claims, abstract, and drawings—provides sufficient information for a person having ordinary skill in the art to practice the invention disclosed and claimed herein. Any measures necessary to practice this invention are well within the skill of a person having ordinary skill in this art after that person has made a careful study of this disclosure.

Because of this disclosure and solely because of this disclosure, modification of this method and apparatus can become clear to a person having ordinary skill in this particular art. Such modifications are clearly covered by this disclosure.

The invention claimed is:

1. A food container having a tube with a piston mounted in the tube, comprising:
   (a) the piston including a food contact member slidably mounted in the tube;
   (b) the piston also having a hollow handle extending from the food contact member;
   (c) the tube receiving a first food;
   (d) the hollow handle receiving a second food;
   (e) the hollow handle having a closed end and an open end;
   (f) the open end being releasably secured to the food contact member;
   (g) the closed end being outside the tube;
   (h) the hollow handle cooperating with the food contact member in order to close the open end;
   (i) the food contact member having a food side and a pushing side;
   (j) the pushing side including a central holder to support the hollow handle on the food contact member and form the piston; and
   (k) the central holder being secured to the hollow handle;
   (l) the open end having at least one male protuberance thereon;
   (m) the central holder having a tab extending therefrom;
   (n) the tab having at least one aperture; and
   (o) the at least one male protuberance having a matching counterpart with the at least one aperture.

2. The food container of claim 1 further comprising:
   (a) the at least one aperture in the tab being releasable from the at least one male protuberance;
   (b) the at least one protuberance being three protuberances; and
   (c) the at least one aperture being three apertures.

3. The food container of claim 2 further comprising:
   (a) the central holder receiving the open end in a female to male relationship in order to thereby close the open end;
   (b) the piston serving to close a first end of the tube.

4. In a food container having a tube with a piston mounted in the tube, the improvement comprising:
   (a) the food container supporting two separate compartments for a food;
   (b) the piston including a food contact member slidably mounted in the tube;
   (c) the piston also having a hollow handle extending from the food contact member;
   (d) the tube receiving a first food;
   (e) the hollow handle receiving a second food;
   (f) the hollow handle having a closed end and an open end;
   (g) the open end being releasably secured to the food contact member;
   (h) the closed end being outside the tube;
   (i) the hollow handle cooperating with the food contact member in order to close the open end;
   (j) the food contact member having a food side and a pushing side;
   (k) the pushing side including a central holder to support the hollow handle on the food contact member and form the piston;
   (l) the central holder being secured to the hollow handle;
   (m) the open end having at least one male protuberance thereon;
   (n) the central holder having a tab extending therefrom;
   (o) the tab having at least one aperture; and
   (p) the at least one male protuberance having a matching counterpart with the at least one aperture.

5. The food container of claim 4 further comprising:
   (a) the at least one aperture in the tab being releasable from the at least one male protuberance;
   (b) the at least one male protuberance being three protuberances; and
   (c) the at least one aperture being three apertures.

6. The food container of claim 5 further comprising:
   (a) the central holder receiving the open end in a female to male relationship in order to thereby close the open end;
   (b) the piston serving to close a first end of the tube.

7. A method of removing from a food container having a first food compartment and a second food compartment comprising the steps of;
   (a) supporting a first food in a tube;
   (b) supporting a second food in a hollow handle;
   (c) securing the hollow handle to a food contact member in order to form a piston in the tube, the piston being at least adjacent to the food in the tube;
   (d) moving the food contact member in order to consume the first food;
   (e) releasing the hollow handle in order to consume the second food;
   (f) the hollow handle having a closed end and an open end;
   (g) the open end being releasably secured to the food contact members;

(h) the closed end being outside the tube; and
(i) the hollow handle cooperating with the food contact member in order to close the open end;
(j) the food contact member having a food side and a pushing side;
(k) the pushing side including a central holder to support the hollow handle on the food contact member and form the piston;
(l) the central holder being secured to the hollow handle;
(m) the open end having at least one male protuberance thereon;
(n) the central holder having a tab extending therefrom;
(o) the tab having at least one aperture; and
(p) the at least one male protuberance having a matching counterpart with the at least one aperture.

8. The method container of claim 7 further comprising the steps of:
   (a) the at least one aperture in the tab being releasable from the at least one male protuberance;
   (b) the at least one protuberance being three protuberances; and
   (c) the at least one male aperture being three apertures.

9. The method of claim 8 further comprising the steps of:
   (a) the central holder receiving the open end in a female to male relationship in order to thereby close open end;
   (b) the piston serving to close a first end of the tube.

* * * * *